US006207803B1

(12) United States Patent
Gross et al.

(10) Patent No.: US 6,207,803 B1
(45) Date of Patent: Mar. 27, 2001

(54) HUMAN REQUIEM

(75) Inventors: Mitchell S Gross, Wayne; Mark Robert Hurle, Norristown; Kristine Kay Kikly, Linfield, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/233,342

(22) Filed: Jan. 19, 1999

Related U.S. Application Data

(62) Division of application No. 08/881,857, filed on Jun. 24, 1997.
(60) Provisional application No. 60/021,229, filed on Jun. 26, 1996.

(51) Int. Cl.[7] .................................................. C07K 14/435
(52) U.S. Cl. ............................................ 530/358; 530/350
(58) Field of Search .................................. 530/350, 358; 435/7.1, 7.23; 514/2

(56) References Cited

PUBLICATIONS

Gabig et. al., "Requiem: A novel zinc finger gene . . . ", Journal of Biological Chemistry 269: p29515–29519, Nov. 1994.*
GenBank Accession No. U94585.
Gabig, T.G., et al., "Requiem: A Novel Zinc Finger Gene Essential for Apoptosis in Myeloid Cells", *J. Biol. Chem.*, 269(47): 29515–29519, (1994).
GenBank Accession No. U10435.
GenBank Accession No. T13371 polynucleotide.
GenBank Accession No. T13371 polypeptide.
GenBank Accession No. D78482.
Gabig et al. "Requiem: A New $C_2$–$H_2$ Zinc Finger Gene Essential for Programmed Cell Death in Myeloid Cells", Blood, vol. 84 (10 Suppl. 1), pp. 366a, #1448 (1994).
Buchman et al. "Differential splicing creates a diversity of transcripts from a neurospecific developmentally regulated gene encoding a protein with new zinc–finger motifs", Nucleic Acids Research, vol. 20 (21), pp. 5579–5585 (1992).

\* cited by examiner

*Primary Examiner*—David Guzo
*Assistant Examiner*—Gerald G. Leffers, Jr.
(74) *Attorney, Agent, or Firm*—Elizabeth J. Hecht; Ratner & Prestia; William T. King

(57) ABSTRACT

Human REQUIEM polypeptides and DNA (RNA) encoding such REQUIEM and a procedure for producing such polypeptides by recombinant techniques is disclosed. Also disclosed are methods for utilizing such REQUIEM for the treatment of a susceptibility to viral infection, tumorogenesis and to diseases and defects in the control of embryogenesis and tissue homeostasis, and the nucleic acid sequences described above may be employed in an assay for ascertaining such susceptibility. Antagonists against such REQUIEM and their use as a therapeutic to treat Alzheimer's disease, Parkinson's disease, rheumatoid arthritis, septic shock, sepsis, stroke, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, AIDS, myelodysplastic syndromes, aplastic anemia, male pattern baldness, and head injury damage are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding REQUIEM polypeptide and for detecting altered levels of the polypeptide in a host.

3 Claims, 6 Drawing Sheets

REQUIEM nucleic acid sequence (SEQ ID NO: 1) and predicted amino acid sequence (SEQ ID NO: 2)

```
     GGCACGAGGGAACAGGGAAGATGGCGGCTGTGGTGGAAAATGTAGTGAAGCTCCTTGGGG
  1---------+---------+---------+---------+---------+---------+60
     CCGTGCTCCCTTGTCCCTTCTACCGCCGACACCACCTTTTACATCACTTCGAGGAACCCC

M   A   A   V   V   E   N   V   V   K   L   L   G   E -

AGCAGTACTACAAAGATGCCATGGAGCAGTGCCACAATTACAATGCTCGCCTCTGTGCTG
 61---------+---------+---------+---------+---------+---------+120
     TCGTCATGATGTTTCTACGGTACCTCGTCACGGTGTTAATGTTACGAGCGGAGACACGAC

Q   Y   Y   K   D   A   M   E   Q   C   H   N   Y   N   A   R   L   C   A   E -

AGCGCAGCGTGCGCCTGCCTTTCTTGGACTCACAGACCGGAGTAGCCCAGAGCAATTGTT
121---------+---------+---------+---------+---------+---------+180
     TCGCGTCGCACGCGGACGGAAAGAACCTGAGTGTCTGGCCTCATCGGGTCTCGTTAACAA

R   S   V   R   L   P   F   L   D   S   Q   T   G   V   A   Q   S   N   C   Y -

ACATCTGGATGGAAAAGCGACACCGGGGTCCAGGATTGGCCTCCGGACAGCTGTACTCCT
181---------+---------+---------+---------+---------+---------+240
     TGTAGACCTACCTTTTCGCTGTGGCCCCAGGTCCTAACCGGAGGCCTGTCGACATGAGGA

I   W   M   E   K   R   H   R   G   P   G   L   A   S   G   Q   L   Y   S   Y -

ACCCTGCCCGGCGCTGGCGGAAAAAGCGGCGAGCCCATCCCCCTGAGGATCCACGACTTT
241---------+---------+---------+---------+---------+---------+300
     TGGGACGGGCCGCGACCGCCTTTTTCGCCGCTCGGGTAGGGGGACTCCTAGGTGCTGAAA

P   A   R   R   W   R   K   K   R   R   A   H   P   P   E   D   P   R   L   S -

CCTTCCCATCTATTAAGCCAGACACAGACCAGACCCTGAAGAAGGAGGGGCTGATCTCTC
```

Fig. 1A

```
301---------+---------+---------+---------+---------+---------+360
   GGAAGGGTAGATAATTCGGTCTGTGTCTGGTCTGGGACTTCTTCCTCCCCGACTAGAGAG

F   P   S   I   K   P   D   T   D   Q   T   L   K   K   E   G   L   I   S   Q -

AGGATGGCAGTAGTTTAGAGGCTCTGTTGCGCACTGACCCCCTGGAGAAGCGAGGTGCCC
361---------+---------+---------+---------+---------+---------+420
   TCCTACCGTCATCAAATCTCCGAGACAACGCGTGACTGGGGGACCTCTTCGCTCCACGGG

D   G   S   S   L   E   A   L   L   R   T   D   P   L   E   K   R   G   A   P -

CGGATCCCCGAGTTGATGATGACAGCCTGGGCGAGTTTCCTGTGACCAACAGTCGAGCGC
421---------+---------+---------+---------+---------+---------+480
   GCCTAGGGGCTCAACTACTACTGTCGGACCCGCTCAAAGGACACTGGTTGTCAGCTCGCG

D   P   R   V   D   D   D   S   L   G   E   F   P   V   T   N   S   R   A   R -

GAAAGCGGATCCTAGAACCAGATGACTTCCTGGATGACCTCGATGATGAAGACTATGAAG
481---------+---------+---------+---------+---------+---------+540
   CTTTCGCCTAGGATCTTGGTCTACTGAAGGACCTACTGGAGCTACTACTTCTGATACTTC

K   R   I   L   E   P   D   D   F   L   D   D   L   D   D   E   D   Y   E   E -

AAGATACTCCCAAGCGTCGGGGAAAGGGGAAATCCAAGGGTAAGGGTGTGGGCAGTGCCC
541---------+---------+---------+---------+---------+---------+600
   TTCTATGAGGGTTCGCAGCCCCTTTCCCCTTTAGGTTCCCATTCCCACACCCGTCACGGG

D   T   P   K   R   R   G   K   G   K   S   K   G   K   V   G   S   A   R -

GTAAGAAGCTGGATGCTTCCATCCTGGAGGACCGGGATAAGCCCTATGCCTGTGACAATA
601---------+---------+---------+---------+---------+---------+660
   CATTCTTCGACCTACGAAGGTAGGACCTCCTGGCCCTATTCGGGATACGGACACTGTTAT

```
     GTTTCAAACAAAAGCATACCTCGAAAGCGCCCCAGAGAGTTTGTGGAAAACGTTACAAGA
661 ---------+---------+---------+---------+---------+---------+720
     CAAAGTTTGTTTTCGTATGGAGCTTTCGCGGGGTCTCTCAAACACCTTTTGCAATGTTCT

F   K   Q   K   H   T   S   K   A   P   Q   R   V   C   G   K   R   Y   K   N -

ACCGACCAGGCCTCAGTTACCACTATGCCCACTCCCACTTGGCTGAGGAGGAGGGCGAGG
721 ---------+---------+---------+---------+---------+---------+780
     TGGCTGGTCCGGAGTCAATGGTGATACGGGTGAGGGTGAACCGACTCCTCCTCCCGCTCC

R   P   G   L   S   Y   H   Y   A   H   S   H   L   A   E   E   E   G   E   D -

ACAAGGAAGACTCTCAACCACCCACTCCTGTTTCCCAGAGGTCTGAGGAGCAGAAATCCA
781 ---------+---------+---------+---------+---------+---------+840
     TGTTCCTTCTGAGAGTTGGTGGGTGAGGACAAAGGGTCTCCAGACTCCTCGTCTTTAGGT

K   E   D   S   Q   P   P   T   P   V   S   Q   R   S   E   E   Q   K   S   K -

AAAAGGGTCCTGATGGATTGGCCTTGCCCAACAACTACTGTGACTTCTGCCTGGGGGACT
841 ---------+---------+---------+---------+---------+---------+900
     TTTTCCCAGGACTACCTAACCGGAACGGGTTGTTGATGACACTGAAGACGGACCCCCTGA

K   G   P   D   G   L   A   L   P   N   N   Y   C   D   F   C   L   G   D   S -

CAAAGATTAACAAGAAGACGGGACAACCCGAGGAGCTGGTGTCCTGTTCTGACTGTGGCC
901 ---------+---------+---------+---------+---------+---------+960
     GTTTCTAATTGTTCTTCTGCCCTGTTGGGCTCCTCGACCACAGGACAAGACTGACACCGG

K   I   N   K   K   T   G   Q   P   E   E   L   V   S   C   S   D   C   G   R -

GCTCAGGGCATCCATCTTGCCTCCAATTTACCCCCGTGATGATGGCGGCAGTGAAGACAT
961 ---------+---------+---------+---------+---------+--------+1020
     CGAGTCCCGTAGGTAGAACGGAGGTTAAATGGGGCACTACTACCGCCGTCACTTCTGTA

```
      ACCGCTGGCAGTGCATCGAGTGCAAATGTTGCAATATCTGCGGCACCTCCGAGAATGACG
1021 --------+---------+---------+---------+---------+---------+1080
      TGGCGACCGTCACGTAGCTCACGTTTACAACGTTATAGACGCCGTGGAGGCTCTTACTGC

R   W   Q   C   I   E   C   K   C   N   I   C   G   T   S   E   N   D   D -

ACCAGTTGCTCTTCTGTGATGACTGCGATCGTGGCTACCACATGTACTGTCTCACCCCGT
1081 --------+---------+---------+---------+---------+---------+1140
      TGGTCAACGAGAAGACACTACTGACGCTAGCACCGATGGTGTACATGACAGAGTGGGGCA

Q   L   L   F   C   D   D   C   D   R   G   Y   H   M   Y   C   L   T   P S -

CCATGTCTGAGCCCCCTGAAGGAAGTTGGAGCTGCCACCTGTGTCTGGACCTGTTGAAAG
1141 --------+---------+---------+---------+---------+---------+1200
      GGTACAGACTCGGGGGACTTCCTTCAACCTCGACGGTGGACACAGACCTGGACAACTTTC

M   S   E   P   P   E   G   S   W   S   C   H   L   C   L   D   L   L   K E -

AGAAAGCTTCCATCTACCAGAACCAGAACTCCTCTTGATGTGGCCACCCACCTGCTCCCC
1201 --------+---------+---------+---------+---------+---------+1260
      TCTTTCGAAGGTAGATGGTCTTGGTCTTGAGGAGAACTACACCGGTGGGTGGACGAGGGG

K   A   S   I   Y   Q   N   Q   N   S   S   *                              -

GACATATCTAAGGCTGTTTCTCTCCTCCACTTCATATTTCATACCCATCTTTCCCTTCTT
1261 --------+---------+---------+---------+---------+---------+1320
      CTGTATAGATTCCGACAAAGAGAGGAGGTGAAGTATAAAGTATGGGTAGAAAGGGAAGAA

CCTCCTCTCCTTCACAAATCCAGAGAACCTTGGGGTGGTTGTGCCAGCCTGCCTTTGGCA
1321 --------+---------+---------+---------+---------+---------+1380
      GGAGGAGAGGAAGTGTTTAGGTCTCTTGGAACCCCACCAACACGGTCGGACGGAAACCGT
```

Fig. 1D

```
      GCTGCAAGCTGAGGTGGCAGCTCTGACCACCTCTGGCCCCAGGCCCTCCAGGGAGAAAGG
1381 --------+---------+---------+---------+---------+--------+1440
      CGACGTTCGACTCCACCGTCGAGACTGGTGGAGACCGGGGTCCGGGAGGTCCCTCTTTCC

-

AGCAACACACTGCCCCTAGGCGTGCGTGTGGCCCAGTTTCTCTCTGCTCTCCATTAAGTG
1441 --------+---------+---------+---------+---------+--------+1500
      TCGTTGTGTGACGGGGATCCGCACGCACACCGGGTCAAAGAGAGACGAGAGGTAATTCAC

-

CATTCACTCTGCTTGCCTTGGGCCCAGCCCCCTGGTTGATTACAGGGTTCAAGGGA
1501 --------+---------+---------+---------+---------+--------+1556
      GTAAGTGAGACGAACGGAACCCGGGTCGGGGGACCAACTAATGTCCCAAGTTCCCT
```

Fig. 1E

Amino acid sequence homology between REQUIEM and murine requiem

```
  1  MAAVVENVVKLLGEQYYKDAMEQCHNYNARLCAERSVRLPFLDSQTGVAQ   50
                         ||||||||||||||||||||||||||||||
  1  . . . . . . . . . .MEQCHNYNARLCAERSVRLPFLDSQTGVAQ   30

51  SNCYIWMEKRHRGPGLASGQLYSYPARRWRKKRRAHPPEDPRLSFPSIKP  100
     |||||||||||||||||||||||||||||||||||||||||||||||||
 31  SNCYIWMEKRHRGPGLASGQLYSYPARRWRKKRRAHPPEDPRLSFPSIKP   80

101  DTDQTLKKEGLISQDGSSLEALLRTDPLEKRGAPDPRVDDDSLGEFPVSN  150
     |||||||||||||||||||||||||||||||||||||||||||||||||
 81  DTDQTLKKEGLISQDGSSLEALLRTDPLEKRGAPDPRVDDDSLGEFPVSN  130

151  SRARKRILEPDDFLDDLDDEDYEEDTPKRRGKGKSKGKGVGSARKKLDAS  200
     |||||||||||||||||||||||||||||||||||||||||||||||||
131  SRARKRILEPDDFLDDLDDEDYEEDTPKRRGKGKSKGKGVGSARKKLDAS  180

201  ILEDRDKPYACDNSFKQKHTSKAPQRVCGKRYKNRPGLSYHYAHSHLAEE  250
     |||||||||||           :||||||||||||||||||||||||||
181  ILEDRDKPYACD. . . . . .ICGKRYKNRPGLSYHYAHSHLAEE   216

251  EGEDKEDSQPPTPVSQRSEEQKSKKGPDGLALPNNYCDFCLGDSKINKKT  300
     ||||||||·||||||||||||||||||||||||||||||||||||||||
217  EGEDKEDSRPPTPVSQRSEEQKSKKGPDGLALPNNYCDFCLGDSKINKKT  266

301  GQPEELVSCSDCGRSGHPSCLQFTPVMMAAVKTYRWQCIECKCCNICGTS  350
     |||||||||||||||||||||||||||||||||||||||||||||:|||
267  GQPEELVSCSDCGRSGHPSCLQFTPVMMAAVKTYRWQCIECKCCNLCGTS  316

351  ENDDQLLFCDDCDRGYHMYCLTPSMSEPPEGSWSCHLCLDLLKEKASIYQ  400
     |||||||||||||||||||||||||||||||||||||||||||||||||
317  ENDDQLLFCDDCDRGYHMYCLTPSMSEPPEGSWSCHLCLDLLKEKASIYQ  366

401  NQNSS*   406
     ||||||
367  NQNSS*   372
```

Fig. 2

HUMAN REQUIEM

This application is a division of U.S. application Ser. No. 08/881,857, U.S. Pat. No. 5,919,660, filed Jun. 24, 1997, which claims the benefit of U.S. Provisional Application No. 60/021,229, filed Jun. 26, 1996.

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of a human homologue of murine requiem gene, hereinafter referred to as "REQUIEM".

BACKGROUND OF THE INVENTION

Hematopoietic stem cell proliferation, differentiation and apoptosis, are regulated by various growth factors and cytokines (Metcalf, D., *Science* 254, 529–531 (1992) and Vaux et al., *Nature* 335, 440–442 (1988)). Such cells committed to the myeloid lineage express high affinity receptors for GM-CSF1 and IL-3 (Miyajima et al., *Blood* 82,1960–1973 (1993)). Moreover, such cells develop a requirement for GM-CSF or IL-3 to survive and undergo apoptosis in response to GM-CSF or IL-3 deprivation (Williams et al., *Nature* 343, 76–79 (1990)).

Hematopoietic cells are not unique in their requirement for growth factors for survival. Throughout development, cells of all lineages require proper signals to grow and differentiate. Failure to receive these signals often results in death of the cells by apoptosis. Even in the adult organism there is constant renewal and/or maintence of cells that requires growth factors and cytokines. Inappropriate cessation of signals from these growth factors may result in apoptosis thereby causing disfunction or disease.

Several apoptotic genes appear to be conserved in multicellular organisms. For example, the ced-3 gene of *Caenorhabditis elegans* has a family of mammalian homologue cysteine protease, including interleukin-1β-converting enzyme (ICE), Ich-1, CPP32, TX, ICErelIII, and LAP3 (Yuan, et al., *Cell* 75, 641–652 (1993) and Miura, et al., *Cell* 75, 653–660 (1993); Wang, et al., *Cell* 78, 739–750 (1994), Fernandes-Alnemri, et al., *JBC* 269, 30761–30764 (1994), Faucheu, et al., *EMBO J* 14, 1914–1922 (1995), Munday, et al., *JBC* 270, 15870–15876 (1995) and Duan, et al., *JBC* 271, 35013–35035 (1996)). Antagonists of the apoptosis are also conserved, such as, for example, ced-9 of *C. elegans* and its mammalian homologue bcl-2. Molecular control of initiation is less well resolved.

Cell lines that proliferate in response to IL-3 and undergo rapid programmed cell death following IL-3 deprivation can be used for expression cloning systems. Using such a system, genes that antagonize apoptosis may be found. Murine cells have been shown to be useful for this purpose. A murine Requiem gene believed to encode a transcription factor required for apoptosis response following survival factor withdrawal from myeloid cells has been described (Gabig, et al., *JBC* 269, 29515–29519 (1994)).

The present invention provides a human homolog of the Requiem gene and polypeptides encoded therefrom (herein "REQUIEM"). The human sequence contains more 5' sequence than the mouse requiem sequence and has a more 5' start site which is believed to be the correct start site.

SUMMARY OF THE INVENTION

Toward these ends, and others, it is an object of the present invention to provide polypeptides, inter alia, that have been identified as novel REQUIEM by homology between the amino acid sequence set out in FIGS. 1A, 1B, 1C, 1D and 1E and known amino acid sequences of other proteins such as those sequences set out in FIG. 2.

It is a further object of the invention, moreover, to provide polynucleotides that encode REQUIEM, particularly polynucleotides that encode the polypeptide herein designated REQUIEM.

In a particularly preferred embodiment of this aspect of the invention the polynucleotide comprises the region encoding human REQUIEM as set forth in FIGS. 1A, 1B, 1C, 1D and 1E.

In accordance with this aspect of the present invention there is provided an isolated nucleic acid molecule encoding a mature polypeptide expressed by the human cDNA of FIGS. 1A, 1B, 1C and 1E encoding the polypeptide in FIGS. 1A, 1B, 1C, 1D and 1E.

In accordance with this aspect of the invention there are provided isolated nucleic acid molecules encoding human REQUIEM, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human REQUIEM.

It also is an object of the invention to provide REQUIEM polypeptides, particularly human REQUIEM polypeptides, that may be employed for therapeutic purposes, for example, to treat viral infection, as an anti-tumor agent and to control embryonic development and tissue homeostasis.

In accordance with this aspect of the invention there are provided novel polypeptides of human origin referred to herein as REQUIEM as well as biologically, diagnostically or therapeutically useful fragments, variants and derivatives thereof, variants and derivatives of the fragments, and analogs of the foregoing.

Among the particularly preferred embodiments of this aspect of the invention are variants of human REQUIEM encoded by naturally occurring alleles of the human REQUIEM gene.

It is another object of the invention to provide a process for producing the aforementioned polypeptides, polypeptide fragments, variant and derivatives, fragments of the variants and derivatives, and analogs of the foregoing.

In a preferred embodiment of this aspect of the invention there are provided methods for producing the aforementioned REQUIEM polypeptides comprising culturing host cells having expressibly incorporated therein an exogenously-derived human REQUIEM-encoding polynucleotide under conditions for expression of human REQUIEM in the host and then recovering the expressed polypeptide. REQUIEM may also be purified from natural sources using any of many well known techniques.

In accordance with another object the invention there are provided products, compositions, processes and methods that utilize the aforementioned polypeptides and polynucleotides for research, biological, clinical, diagnostic and therapeutic purposes, inter alia.

In accordance with certain preferred embodiments of this aspect of the invention, there are provided products, compositions and methods, inter alia, for, among other things: assessing REQUIEM expression in cells by determining REQUIEM polypeptides or REQUIEM-encoding mRNA; as an antiviral agent, an anti-tumor agent and to control embryonic development and tissue homeostasis invitro, ex vivo or in vivo by exposing cells to REQUIEM polypeptides or polynucleotides as disclosed herein; assaying genetic variation and aberrations, such as defects, in REQUIEM genes; and administering a REQUIEM polypeptide or polynucleotide to an organism to augment REQUIEM function or remediate REQUIEM dysfunction. Agonists targeted to defective cellular proliferation, including, for example, cancer cells and solid tumor cells may be used for the treatment of these diseases. Such targeting may be achieved via gene therapy of using antibody fusions. Agonists may also be used to treat follicular lymphomas, carcinomas associated with p53 mutations, autoimmune disorders, such as, for example, SLE, immune-mediated glomerulonephritis; and hormone-dependent tumors, such as, for example, breast cancer, prostate cancer and ovary cancer; and viral infections, such as, for example, herpesviruses, poxviruses and adenoviruses.

In accordance with certain preferred embodiments of this and other aspects of the invention there are provided probes that hybridize to human REQUIEM sequences.

In certain additional preferred embodiments of this aspect of the invention there are provided antibodies against REQUIEM polypeptides. In certain particularly preferred embodiments in this regard, the antibodies are highly selective for human REQUIEM.

In accordance with another aspect of the present invention, there are provided REQUIEM agonists. Among preferred agonists are molecules that mimic REQUIEM, that bind to REQUIEM-binding molecules or receptor molecules, and that elicit or augment REQUIEM-induced response. Also among preferred agonists are molecules that interact with REQUIEM or REQUIEM polypeptides, or with other modulators of REQUIEM activities and/or gene expression, and thereby potentiate or augment an effect of REQUIEM or more than one effect of REQUIEM.

In accordance with yet another aspect of the present invention, there are provided REQUIEM antagonists. Among preferred antagonists are those which mimic REQUIEM so as to bind to REQUIEM receptor or binding molecules but not elicit a REQUIEM-induced response or more than one REQUIEM-induced response. Also among preferred antagonists are molecules that bind to or interact with REQUIEM so as to inhibit an effect of REQUIEM or more than one effect of REQUIEM or which prevent expression of REQUIEM.

In a further aspect of the invention there are provided compositions comprising a REQUIEM polynucleotide or a REQUIEM polypeptide for administration to cells in vitro, to cells ex vivo and to cells in vivo, or to a multicellular organism. In certain particularly preferred embodiments of this aspect of the invention, the compositions comprise a REQUIEM polynucleotide for expression of a REQUIEM polypeptide in a host organism for treatment of disease. Particularly preferred in this regard is expression in a human patient for treatment of a dysfunction associated with aberrant endogenous activity of REQUIEM.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A, 1B, 1C, 1D and 1E show the nucleic acid and predicted amino acid sequence of human REQUIEM (SEQ ID NOS: 1 and 2).

FIG. 2 shows a sequence alignment of human REQUIEM (top) (SEQ ID NO: 2) and a known member of murine requiem (bottom) (SEQ ID NO: 5).

GLOSSARY

The following illustrative explanations are provided to facilitate understanding of certain teams used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 $\mu$g of plasmid or DNA fragment is digested with about 2 units of enzyme in about 20 $\mu$l of reaction buffer. For the purpose of isolating DNA fragments for plasmid construction, typically 5 to 50 $\mu$g of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

IDENTITY or SIMILARITY, as known in the art, are relationships between two polypeptides as determined by comparing the amino acid sequence and its conserved amino acid substitutes of one polypeptide to the sequence of a second polypeptide. Moreover, also known in the art is "identity" which means the degree of sequence relatedness between two polypptide or two polynucleotides sequences as determined by the identity of the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991). While there exist a number of methods to measure identity and similarity between two polynucleotide or polypeptide sequences, the terms "identity" and "similarity" are well known to skilled artisans (*Sequence Analysis in Molecular Biology*, von Heinje, G., Academic Press, 1987; *Sequence Analysis Primer*, Gribskov, M. and Devereux, J., eds., M. Stockton Press, New York, 1991; and Carillo, H., and Lipman, D., SIAM *J. Applied Math.*, 48: 1073 (1988). Methods commonly employed to determine identity or similarity between two sequences include, but are not limited to disclosed in Carillo, H., and Lipman, D., SIAM *J. Applied Math.*, 48: 1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *MOLECULAR CLONING, A LABORATORY MANUAL*, 2nd Ed.; Cold Spring Harbor Laboratory Press, Cold Spring Harbor, N.Y. (1989) ("Sambrook") and Maniatis et al., pg. 146, as cited below.

OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art.

Starting plasmids disclosed herein are either commercially available, publicly available on an unrestricted basis, or can be constructed from available plasmids by routine application of well known, published procedures. Many plasmids and other cloning and session vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other posttranslational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., Analysis for protein modifications and nonprotein cofactors, Meth. Enzymol. 182: 626–646 (1990) and Rattan et al., *Protein Synthesis: Posttranslational Modifications and Aging*, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with REQUIEM polypeptides of the present invention, including not only classic receptors, which are preferred, but also other molecules that specifically bind to or interact with polypeptide of the invention (which also may be referred to as "binding molecules" and "interaction molecules," respectively and as "REQUIEM binding molecules" and "REQUIEM interaction molecules." Binding between polypeptide of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to novel REQUIEM polypeptides and polynucleotides, among other things, as described in greater detail below. In particular, the invention relates to polypeptides and polynucleotides of a novel human REQUIEM, which is related by amino acid sequence homology to murine requiem polypeptide. The invention relates especially to REQUIEM having the nucleotide and amino acid sequences set out in FIGS. 1A, 1B, 1C, 1D and 1E. It will be appreciated that the nucleotide and amino acid sequences set out in FIGS. 1A, 1B, 1C, 1D and 1E were obtained by sequencing the cDNA obtained from a human cDNA library made from human cerebellum.

Polynucleotides

In accordance with one aspect of the present invention, there are provided isolated polynucleotides which encode the REQUIEM polypeptide having the deduced amino acid sequence of FIGS. 1A, 1B, 1C, 1D and 1E.

In accordance with another aspect of the present invention, there are provided isolated polynucleotides which encode the REQUIEM polypeptide having the deduced amino acid sequence of FIGS. 1A, 1B, 1C, 1D and 1E.

Using the information provided herein, such as the polynucleotide primers sequences set out in Example 1, a polynucleotide of the present invention encoding human REQUIEM polypeptide may be obtained using standard cloning and screening procedures, such as those for cloning cDNAs using mRNA from cells from microvascular endothelial tissue as starting material. Illustrative of the invention, the polynucleotide of the invention was discovered as described in Example 1. REQIUEM can also be obtained from other tissues and cDNA libraries, for example, libraries derived from cells of human tissue and cell lines such as, endothelial cells and CEM cells.

Human REQUIEM of the invention is structurally related to other proteins of the requiem family, as shown by the results of sequencing the cDNA encoding human REQUIEM in FIGS. 1A, 1B, 1C, 1D and 1E. The cDNA of derived using the primers set forth in Example 1 was obtained as described in Example 1. The polypeptide of FIGS. 1A, 1B, 1C, 1D and 1E is a protein has a deduced molecular weight of about 45 kDa.

Polynucleotides of the present invention may be in the form of RNA, such as mRNA, or in the form of DNA, including, for instance, cDNA and genomic DNA obtained by cloning or produced by chemical sync techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide of FIGS. 1A, 1B, 1C, 1D and 1E. It also may be a polynucleotide with a different sequence, which, as a result of the redundancy (degeneracy) of the genetic code, encodes the polypeptide of the DNA of FIGS. 1A, 1B, 1C, 1D and 1E.

Polynucleotides of the present invention which encode the polypeptide of FIGS. 1A, 1B, 1C, 1D and 1E may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Also provided is mature REQUIEM processed from its precursor molecule, via autocatalysis or by other enzymes, to produce two subunites, which form an active heterodimer (both subunits) or tetramer (two sets heterodimers). Thus, for instance, the polypeptide may be fused to a marker sequence, such as a peptide, which a purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci.,* USA 86: 821–824 (1989), for instance, hexa-histidine provides for convenient purification of the fusion protein. The HA tag corresponds to an epitope derived of influenza hemagglutinin pain, which has been described by Wilson et al., *Cell* 37: 767 (1984), for instance.

In accordance with the foregoing, the term "polynucleotide encoding a polypeptide" as used herein encompasses polynucleotides which include a sequence encoding a polypeptide of the present invention, particularly the human REQUIEM having the amino acid sequence set out in FIGS. 1A, 1B, 1C, 1D and 1E. The term encompasses polynucleotides that a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIGS. 1A, 1B, 1C, 1D and 1E. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly prefaced embodiments of the invention in this regard are polynucleotides encoding polypeptides having the amino acid sequence of REQUIEM set out in FIGS. 1A, 1B, 1C, 1D and 1E; variant, analogs, derivatives and fragments thereof, and fragments of the variants, analogs and derivatives.

Further particularly preferred in this regard are polynucleotides encoding REQUIEM variants, analogs, derivatives and fragments, and variants, analogs and derivatives of the fragments, which have the amino acid sequence of the REQUIEM polypeptide of FIGS. 1A, 1B, 1C, 1D and 1E in which several, a few, 5 to 10, 1 to 5, 1 to 3, 2, 1 or no amino acid residues are substituted, deleted or added, in any combination. Especially preferred among these are substitutions, additions and deletions, which do not alter the properties and activities of the REQUIEM. Also especially preferred in this regard are conservative substitutions. Most highly preferred are polynucleotides encoding polypeptides having the amino acid sequence of FIGS. 1A, 1B, 1C, 1D and 1E, without substitutions.

Further preferred embodiments of the invention are polynucleotides that are at least 70% identical to a polynucleotide encoding the REQUIEM polypeptide having the amino acid sequence set out in FIGS. 1A, 1B, 1C, 1D and 1E, and polynucleotides which are complementary to such polynucleotides. Alternatively, most highly preferred are polynucleotides that comprise a region that is at least 80% identical to a polynucleotide encoding the REQUIEM polypeptide of the human cDNA and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the cDNA of FIGS. 1A, 1B, 1C, 1D and 1E.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genonic DNA to isolate full-length cDNAs and genomic clones encoding REQUIEM and to isolate cDNA and genomic clones of other genes that have a high sequence similarity to the human REQUIEM gene. Such probes generally will comprise at least 15 bases. Preferably, such probes will have at least 30 bases and may have at least 50 bases. Particularly preferred probes will have at least 30 bases and will have 50 bases or less.

For example, the coding legion of the REQUIEM gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preprotein, which is a precursor to a proprotein, having a leader sequence and one or more prosequences, which generally are removed during processing steps that produce active and mature forms of the polypeptide.

Polypeptides

The present invention further relates to a human REQUIEM polypeptide which has the deduced amino acid sequence of FIGS. 1A, 1B, 1C, 1D and 1E.

The invention also relates to fragments, analogs and derivatives of these polypeptides. The terms "fragment,"

"derivative" and "analog" when referring to the polypeptide of FIGS. 1A, 1B, 1C, 1D and 1E, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIGS. 1A, 1B, 1C, 1D and 1E may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (ii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of REQUIEM set out in FIGS. 1A, 1B, 1C, 1D and 1E, variants, analogs, derivatives and fragments thereof, and variants, analogs and derivatives of the fragments. Alternatively, particularly preferred embodiments of the invention in this regard are polypeptides having the amino acid sequence of the REQUIEM, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the REQUIEM polypeptide of FIGS. 1A, 1B, 1C, 1D and 1E, in which several, a few, 5 to 10, 1 to 5, 1 to 3, 2, 1 or no amino acid residues are substituted, deleted or added, in any combination. Especially preferred among these are substitutions, additions and deletions, which do not alter the properties and activities of the REQUIEM. Also especially preferred in this regard are conservative substitutions. Most highly preferred are polypeptides having the amino acid sequence of FIGS. 1A, 1B, 1C, 1D and 1E without substitutions.

The polypeptides and polynucleotides of the present invention are preferably provided in an isolated form, and preferably are purified to homogeneity.

The polypeptides of the present invention include the polypeptide of FIGS. 1A, 1B, 1C, 1D and 1E (in particular the mature polypeptide) as well as polypeptides which have at least 80% identity to the polypeptide of FIGS. 1A, 1B, 1C, 1D and 1E and more preferably at least 90% similarity (more preferably at least 90% identity) to the polypeptide of FIGS. 1A, 1B, 1C, 1D and 1E and still more preferably at least 95% similarity (still more preferably at least 95% identity) to the polypeptide of FIGS. 1A, 1B, 1C, 1D and 1E and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of REQUIEM, most particularly fragments of the REQUIEM having the amino acid set out in FIGS. 1A, 1B, 1C, 1D and 1E, and fragments of variants and derivatives of the REQUIEM of FIGS. 1A, 1B, 1C, 1D and 1E.

In this regard a fragment is a polypeptide having an amino acid sequence that entirely is the same as part but not all of the amino acid sequence of the aforementioned REQUIEM polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a REQUIEM polypeptide of the present comprised within a precursor polypeptide designed for expression in a host and having heterologous pre and pro-polypeptide regions fused to the amino terminus of the REQUIEM fragment and an additional region fused to the carboxyl terminus of the fragment. Therefore, fragments in one aspect of the meaning intended herein, refers to the portion or portions of a fusion polypeptide or fusion protein derived from REQUIEM.

As representative examples of polypeptide fragments of the invention, there may be mentioned those which have from about 5–15, 10–20, 15–40, 30–55, 41–65, 41–80, 41–90, 50–100, 75–100, 90–115, 100–125, and 110–113 amino acids long.

In this context about includes the particularly recited range and ranges larger or smaller by several, a few, 5, 4, 3, 2 or 1 amino acid at either extreme or at both extremes. For instance, about 40–90 amino acids in this context means a polypeptide fragment of 40 plus or minus several, a few, 5, 4, 3, 2 or 1 amino acids to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–65, 41–80, 41–90, 50–100, 75–100, 90–115, 100–125, and 110–113 amino acids long.

Among especially preferred fragments of the invention are truncation mutants of REQUIEM. Truncation mutants include REQUIEM polypeptides having the amino acid sequence of FIGS. 1A, 1B, 1C, 1D and 1E, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of REQUIEM. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of REQUIEM.

Among highly preferred fragments in this regard are those that comprise regions of REQUIEM that combine several structural features, such as several of the features set out above. In this regard, the regions defined by the residues about 10 to about 20, about 40 to about 50, about 70 to about 90 and about 100 to about 113 of FIGS. 1A, 1B, 1C, 1D and 1E, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of REQUIEM. Most highly preferred in this regard are fragments that have a chemical, biological or other activity of REQUIEM, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIG. 2, which includes murine requiem polypeptide. Among particularly preferred fragments in these regards are truncation mutants, as discussed above.

It will be that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above. Preferred polynucleotides fragments may be derived from the sequences of FIGS. 1A, 1B, 1C, 1D and 1E.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as simian virus 40 ("SV40"), vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, induction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the gpt promoter, the lambda PR, PL promoters and the trp promoter.

Among known eukaryotic promoters suitable in this regard are the cytomegalovirus ("CMV") immediate early promoter, the HSV thymidine kinase promoter, the early and late SV40 promoters, the promoters of retroviral LTRs, such as those of the Rous sarcoma virus ("RoSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. *BASIC METHODS IN MOLECULAR BIOLOGY*, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., cited above.

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trp1 gene of *S. cerevisiae*.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome biding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, a region may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can be employed for expression, as well. Examples of mammalian expression systems include the COS-6 lines of monkey kidney fibroblast, described in Gluzman et al., *Cell* 23: 175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The REQUIEM polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

REQUIEM polynucleotides and polypeptides may be used in accordance with the present invention for a variety of applications, particularly those that make use of the chemical and biological properties of REQUIEM. Additional applications relate to diagnosis and to treatment of disorders of cells, tissues and organisms. These aspects of the invention are illustrated further by the following discussion.

Polynucleotide Assays

This invention is also related to the use of the REQUIEM polynucleotides to detect complementary polynucleotides such as, for example, as a diagnostic reagent. Detection of a mutated form of REQUIEM associated with a dysfunction will provide a diagnostic tool that can add or define a diagnosis of a disease or susceptibility to a disease which results from under-expression over-expression or altered expression of REQUIEM. Individuals carrying mutations in the human REQUIEM gene may be detected at the DNA level by a variety of technique. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., *Nature,* 324: 163–166 (1986)). RNA or cDNA may also be used in the same ways. As an example, PCR primers complementary to the nucleic acid encoding REQUIEM can be used to identify and analyze REQUIEM expression and mutations. For example, deletions and insertions can be detected by a change in size of the amplified product in comparison to the normal genotype. Point mutations can be identified by hybridizing amplified DNA to radiolabeled REQUIEM RNA or alternatively, radiolabeled REQUIEM antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science,* 230: 1242 (1985)).

Sequence changes at specific locations also may be revealed by nuclease protection assays, such as RNase and S1 protection or the chemical cleavage method (e.g., Cotton et al., *Proc. Natl. Acad. Sci., USA,* 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

In accordance with a further aspect of the invention, there is provided a process for determining disease associated with viral infection, tumorogenesis and to control embryogenesis and tissue homeostasis. Diseases associated with viral infection, tumorogenesis and to control embryogenesis and tissue homeostasis, or a susceptibility to viral infection, tumorogenesis and to disease and defects in the control of control of embryogenesis and tissue homeostasis. Thus, a mutation in REQUIEM indicates a susceptibility to viral infection, tumorogenesis and to diseases and defects in the control embryogenesis and tissue homeostasis, and the nucleic acid sequences described above may be employed in an assay for ascertaining such susceptibility. Thus, for example, the assay may be employed to determine a mutation in a human REQUIEM protein as herein described, such as a deletion, truncation, insertion, frame shift, etc., with such mutation being indicative of a susceptibility to viral infection, tumorogenesis and to diseases and defects in the control of embryogenesis and tissue homeostasis.

A mutation may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the REQUIEM protein of the invention. The primer sequence is generally comprised of at least 15 consecutive bases, and may contain at least 30 or even 50 consecutive bases.

Individuals carrying mutations in the gene of the present invention may also be detected at the DNA level by a variety of techniques. Nucleic acids for diagnosis may be obtain from a patient's cells, including but not limited to blood, urine, saliva, tissue biopsy and autopsy material. The genomic DNA may be used directly for detection or may be amplified enzymatically by using PCR (Saiki et al., *Nature*, 324:163–166 (1986) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding REQUIEM can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Primers, selected by well known methods, may be used for amplifying REQUIEM cDNA isolated from a sample derived from a patient. The invention also provides the primers selected with 1, 2, 3 or 4 nucleotides removed from the 5' and/or the 3' end. The primers may be used to amplify the gene isolated from the patient such that the gene may then be subject to various techniques for elucidation of the DNA sequence. In this way, mutations in the DNA sequence may be diagnosed.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., *PNAS, USA* 85:4397–4401(1985)).

Thus, the detection of a specific DNA sequence and/or quantitation of the level of the sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. The invention provides a process for diagnosing or detecting, disease, particularly Alzheimer's disease, Parkinson's disease, rheumatoid arthritis, septic shock, sepsis, stroke, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, AIDS, myelodysplastic syndromes, aplastic anemia, male pattern baldness, and head injury damage, as well as a susceptibility to viral infection and cancer, an to detect aberrant control of embryonic development and tissue homeostasis, comprising determining from a sample derived from a patient altered expression of polynucleotide having the sequence of FIGS. 1A, 1B, 1C, 1D and 1E as compared to normal control samples. Expression of polynucleotide can be measured using any on of the methods well known in the art for the quantation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Fluorescence in situ hybridization (FISH) of a cDNA clone to a metaphase chromosomal spread can be used to provide a precise chromosomal location.

As an example of how this is performed, REQUIEM DNA is digested and purified with QIAEX II DNA purification kit (QIAGEN, Inc., Chatsworth, Calif.) and ligated to Super Cos1 cosmid vector (STRATAGENE, La Jolla, Calif.). DNA is purified using Qiagen Plasmid Purification Kit (QIAGEN Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinilation is detected with GENE-TECT Detection System (CLONTECH Laboratories, Inc. Palo Alto, Calif.). In situ Hybridization is performed on slides using ONCOR light Hybridization Kit (ONCOR, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with $10^{-6}$ M methotrexate for 17 hours and washed twice with unsupplemented RPMI. Cells are incubated with $10^{-3}$ M thymidine for 7 hours. The cells are arrested in metaphase after 20 minutes incubation with colcemid (0.5 µg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and aid dried. Hybridization is performed by adding 100 ng of probe suspended in 10 ml of hybridization mix (50% formamide, 2×SSC, 1% dextran sulfate) with blocking human placental DNA 1 µg/ml), Probe mixture is denatured for 10 minutes in 70° C. water bath and incubated for 1 hour at 37° C., before placing on a prewarmed (37° C.) slide, which is previously denatured in 70% formamide/2×SSC at 70° C., and dehydrated in ethanol series, chilled to 4° C.

Slides are incubated for 16 hours at 37° C. in a humidified chamber. Slides am washed in 50% formamide/2×SSC for 10 minutes at 41° C. and 2×SSC for 7 minutes at 37° C. Hybridization probe is by incubation of the slides with FITC-Avidin (ONCOR, Gaithersberg, Md.), according to the manufacturer protocol. Chromosomes are counterstained with propridium iodine suspended in mounting medium. Slides are visualized using a Leitz ORTHOPLAN 2-epifluorescence microscope and five computer images are taken using Imagenetics Computer and MacIntosh printer.

Once a sequence has been mapped to a precise chromosomal location, the physical position of the sequence on the chromosome can be correlated with genetic map data. Such data are found, for example, in V. McKusick, *Mendelian Inheritance in Man* (publicly available on line via computer). The relationship between genes and diseases that have been mapped to the same chromosomal region are then identified through linkage analysis using well known methods.

Unless otherwise stated, transformation was performed as described in the method of Graham, F. and Van der Eb, A., *Virology*, 52:456–457 (1973).

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a REQUIEM gene. This can be accomplished using a variety of well known techniques and libraries, which generally are available commercially. The genomic DNA is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., *HUMAN CHROMOSOMES: A MANUAL OF BASIC TECHNIQUES*, Pergamon Press, New York (1988).

Once a sequence has been mapped to a precise chromosomal location, the physical position of the sequence on the chromosome can be correlated with genetic map data. Such data are found, for example, in V. McKusick, *MENDELIAN INHERITANCE IN MAN* (publicly available on line via computer). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb).

Polypeptide Assays

The present invention also relates to a diagnostic assays such as quantitative and diagnostic assays for detecting levels of REQUIEM protein in cells and tissues, including determination of normal and abnormal levels. Thus, for instance, a diagnostic assay in accordance with the invention for detecting over-expression of REQUIEM protein compared to normal control tissue samples may be used to detect the presence of a tumor, for example. Assay techniques that can be used to determine levels of a protein, such as an REQUIEM protein of the present invention, in a sample derived from a host are well-known to those of skill in the art. Such assay methods include radioimmunoassays, competitive-binding assays, Western Blot analysis and ELSA assays. Among these ELISAs frequently are preferred. An ELISA assay initially comprises preparing an antibody specific to REQUIEM, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any REQUIEM proteins attached to the polystyrene dish. Unbound monoclonal antibody is washed out with buffer. The reporter antibody linked to horseradish peroxidase is placed in the dish resulting in binding of the reporter antibody to any monoclonal antibody bound to REQUIEM. Unattached reporter antibody is then washed out. Reagents for peroxidase activity, including a colorimetric substrate are then added to the dish. Immobilized peroxidase, linked to REQUIEM through the primary and secondary antibodies, produces a colored reaction product. The amount of color developed in a given time period indicates the amount of REQUIEM protein present in the sample. Quantitative results typically are obtained by reference to a standard curve.

A competition assay may be employed wherein antibodies specific to REQUIEM attached to a solid support and labeled REQUIEM and a sample derived from the host are passed over the solid support and the amount of label detected attached to the solid support can be correlated to a quantity of REQUIEM in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature* 256: 495–497 (1975), the trioma technique, the human B-cell hybridoma technique (Kozbor et al., *Immunology Today* 4: 72 (1983) and the EBV-hybridoma technique to produce human monoclonal antibodies (Cole et al., pg. 77–96 in *MONOCLONAL ANTIBODIES AND CANCER THERAPY,* Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against REQUIEM may be employed to inhibit the action of such REQUIEM polypeptides, for example, in the treatment of Alzheimer's disease, Parkinson's disease, rheumatoid arthritis, septic shock, sepsis, stroke, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cerebellar degeneration, ischemic injury, myocardial infarction, AIDS, myelodysplastic syndromes, aplastic anemia, male pattern baldness, and head injury damage.

REQUIEM Binding Molecules and Assay

This invention also provides a method for identification of molecules, such as receptor molecules, that bind REQUIEM. Genes encoding proteins that bind REQUIEM, such as receptor proteins, can be identified by numerous methods known to those of skill in the art, for example, ligand panning and FACS sorting. Such methods are defined in many laboratory manuals such as, for instance, Coligan et al., *Current Protocols in Immunology* 1(2): Chapter 5 (1991).

For instance, expression cloning may be employed for this purpose. To this end polyadenylated RNA is prepared from a cell responsive to REQUIEM, a cDNA library is created from this RNA, the library is divided into pools and the pools are transfected individually into cells that are not responsive to REQUIEM. The transfected cells then are exposed to labeled REQUIEM. (REQUIEM can be labeled by a variety of well-known techniques including standard methods of radio-iodination or inclusion of a recognition site for a site-specific protein kinase.) Following exposure, the cells are fixed and binding of REQUIEM is determined. These procedures conveniently are carried out on glass slides.

Pools are identified of cDNA that produced REQUIEM binding cells. Sub-pools are prepared from these positives, transfected into host cells and screened as described above. Using an iterative sub-pooling and re-screening process, one or more single clones that encode putative binding molecule, such as a receptor molecule, can be isolated.

Alternatively a labeled ligand can be photoaffinity linked to a cell exact, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess REQUIEM binding capacity of REQUIEM binding molecules, such as receptor molecules, in cells or in cell-free preparations.

Agonists and Antagonists—Assays and Molecules

The invention also provides a method of screening compounds to identify those which enhance or block the action of REQUIEM on cells, such as its interaction with REQUIEM-binding molecules such as receptor molecules. An agonist is a compound which increases the natural biological functions of REQUIEM or which functions in a manner similar to REQUIEM, while antagonists decrease or eliminate such functions.

For example, a cellular compartment, such as a membrane or a preparation thereof, such as a membrane-preparation, may be prepared from a cell that expresses a molecule that binds REQUIEM, such as a molecule of a signaling or regulatory pathway modulated by REQUIEM. The preparation is incubated with labeled REQUIEM in the absence or the presence of a candidate molecule which may be a REQUIEM agonist or antagonist. The ability of the candidate molecule to bind the binding molecule is reflected in decreased binding of the labeled ligand. Molecules which bind gratuitously, i.e., without inducing the effects of REQUIEM on binding the REQUIEM binding molecule, are most likely to be good antagonists. Molecules that bind well and elicit effects that are the same as or closely related to REQUIEM are agonists.

REQUIEM-like effects of potential agonists and antagonists may by measured, for instance, by determining activity of a second messenger system following interaction of the candidate molecule with a cell or appropriate cell preparation, and comparing the effect with that of REQUIEM or molecules that elicit the same effects as REQUIEM. Second messenger systems that may be useful in this regard include but are not limited to AMP guanylate cyclase, ion channel or phosphoinositide hydrolysis second messenger systems.

Another example of an assay for REQUIEM antagonists is a competitive assay that combines REQUIEM and a potential antagonist with membrane-bound REQUIEM receptor molecules or recombinant REQUIEM receptor molecules under appropriate conditions for a competitive inhibition assay. REQUIEM can be labeled, such as by radioactivity, such that the number of REQUIEM molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing REQUIEM-induced activities, thereby preventing the action of REQUIEM by excluding REQUIEM from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules. Antoher antagonist is an oligopeptide comprising the cleavage site recognition motif for REQUIEM.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); *OLIGODEOXY-NUCLEOTIDES AS ANTISENSE INHIBITORS OF GENE EXPRESSION,* CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide from about 10 to 40 base pairs in length. A DNA oligonucleotide is designed to be complementary to a region of the gene involved in transcription thereby preventing transcription and the production of REQUIEM. The antisense RNA oligonucleotide hybridizes to the mRNA in vivo and blocks translation of the mRNA molecule into REQUIEM polypeptide. The oligonucleotides described above can also be delivered to cells such that the antisense RNA or DNA may be expressed in vivo to inhibit production of REQUIEM.

Agonists targeted to defective cellular proliferation, including, for example, cancer cells and solid tumor cells may be used for the treatment of these diseases. Such targeting may be achieved via gene therapy of using antibody fusions.

Agonists may also be used to treat follicular lymphomas, carcinomas associated with p53 mutations, autoimmune disorders, such as, for example, SLE, immune-mediated glomerulonephritis; and hormone-dependent tumors, such as, for example, breast cancer, prostate cancer and ovary cancer; and viral infections, such as, for example, herpesviruses, poxviruses and adenoviruses.

The antagonists may be employed in a composition with a pharmaceutically acceptable carrier, e.g., as hereinafter described.

The antagonists may be employed for instance to inhibit the action of REQUIEM polypeptides, for example, in the treatment of Alzheimer's disease, Parkinson's disease, rheumatoid arthritis, septic shock, sepsis, stroke, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, AIDS, myelodysplastic syndromes, aplastic anemia, male pattern baldness, and head injury damage.

The antagonists may be employed in a composition with a pharmaceutically acceptable carrier, e.g., as hereinafter described.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filed with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 mg/kg body weight per day. Preferably, in most cases, dose is from about 10 µg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The REQUIEM polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the presenst invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter, and the CMV promoter described in Miller et al., *Biotechniques* 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter, or heterologous promoters, such as the CMV promoter; the respiratory syncytial virus ("RSV") promoter; inducible promoters, such as the MMT promoter, the metallothionein promoter; heat shock promoters; the albumin promoter, the ApoAI promoter, human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transducer packaging cell lines to form producer cell lines. Examples of packaging cells which may be transfected include, but are not limited to, the PE501, PA317, Ψ-2, Ψ-AM, PA12, T19-14X, VT-19-17-H2, YCRE, YCRIP, GP+E-86, GP+envAm12, and DAN cell lines as described in Miller, A., *Human Gene Therapy* 1: 5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., cited above.

All parts or amounts set out in the following examples are by weight, unless otherwise specified.

Unless otherwise stated size separation of fragments in the examples below was carried out using techniques of agarose and polyacrylamide gel electrophoresis ("PAGE") in Sambrook and numerous other referees such as, for instance, by Goeddel et al., *Nucleic Acids Res.* 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 μg of DNA.

Example 1

Expression and Purification of Human REQUIEM using Bacteria

The DNA sequence encoding human REQUIEM in the polynucleotide of the cDNA library was amplified using PCR oligonucleotide primers specific to the amino acid carboxyl terminal sequence of the human REQUIEM protein and to vector sequences 3' to the gene. Additional nucleotides containing restriction sites to facilitate cloning were added to the 5' and 3' sequences respectively.

The 5' oligonucleotide primer had the sequence 5' ATAACGA<u>GAATTC</u>ATGGCGGCTGTGGTGGAAAATG 3' (SEQ ID NO:3) containing the underlined EcoRI restriction site, which encodes a start AUG, followed by 1220 nucleotides of the human REQUIEM coding sequence set out in FIGS. 1A, 1B, 1C, 1D and 1E beginning with the first base of the first codon.

The 3' primer had the sequence 5' ACGTCTAGA <u>GATATC</u>CACATCAAGAGGAGTTCTGG 3' (SEQ ID NO:4) containing the underlined EcoRV restriction site followed by 20 nucleotides complementary to the last 20 nucleotides of the REQUIEM coding sequence set out in FIGS. 1A, 1B, 1C, 1D and 1E, including the stop codon.

The restrictions sites were convenient to restriction enzyme sites in the bacterial expression vectors pQE-9 which were used for bacterial expression in these examples. (Qiagen, Inc. Chatsworth, Calif. pQE-9 encodes ampicillin antibiotic resistance ("Amp'") and contains a bacterial origin of replication ("ori"), an IPTG inducible promoter, a ribosome binding site ("RBS"), a 6-His tag and restriction enzyme sites.

The amplified human REQUIEM DNA and the vector pQE-9 both were digested with EcoRI and EcoRV and the digested DNAs then were ligated together. Insertion of the REQUIEM DNA into the EcoRI and EcoRV restricted vector placed the REQUIEM coding region downstream of and operably linked to the vector's IPTG-inducible promoter and in-frame with an initiating AUG appropriately positioned for translation of REQUIEM.

The ligation mixture was transformed into competent *E. coli* cells using standard procedures. Such procedures are described in Sambrook et al., cited above. *E. coli* strain M15/rep4, multiple copies of the plasmid pREP4, which expresses lac repressor and confers kanamycin resistance ("Kan'"), was used in carrying out the illustrative example described here. This strain, which is only one of many that are suitable for expressing REQUIEM, is available commercially from Qiagen.

Transformants were identified by their ability to grow on LB plates in the presence of ampicillin (Amp$^r$ phenotype). Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 ug/m) and kanamycin (25 ug/ml).

The O/N culture was used to inoculate a large culture, at a dilution of approximately 1:100 to 1:250. The cells were grown to an optical density at 600 nm ($OD^{600}$ of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2× phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2× PBS at a concentration of 95 micrograms per mL.

Example 2

Cloning and Expression of Human REQUIEM in a Baculovirus Expression System

The cDNA sequence encoding the full length human REQUIEM protein, in the cDNA library clone is amplified using PCR oligonucleotide primers corresponding to the 5' and 3' sequences of the gene:

The 5' primer has the sequence 5' ATAACGA <u>GAATTC</u>ATGGCGGCTGTGGTGGAAAATG 3' (SEQ ID NO: 3) containing the underlined EcoRI restriction enzyme site followed by 1220 bases of the sequence of REQUIEM of FIGS. 1A, 1B, 1C, 1D and 1E. Inserted into an expression vector, as described below, the 5' end of the amplified fragment encoding human REQUIEM provides an efficient signal peptide. An efficient signal for initiation of translation in eukaryotic cells, as described by Kozak, M., *J. Mol. Biol.* 196: 947–950 (1987) is appropriately located in the vector portion of the construct.

The 3' primer has the sequence 5' ACGTCTAGA <u>GATATC</u>CACATCAAGAGGAGTTCTGG 3' (SEQ ID NO:4) containing the underlined EcoRV restriction followed by nucleotides complementary to the last 20 nucleotides of the REQUIEM coding sequence set out in FIGS. 1A, 1B, 1C, 1D and 1E, including the stop codon.

The amplified fragment is isolated from a 1% agarose gel using a commercially available kit ("Geneclean," BIO 101 Inc., La Jolla, Calif.). The fragment then is digested with EcoRI and EcoRV and again is purified on a 1% agarose gel. This fragment is designated herein F2.

The vector pRG1 is used to express the REQUIEM protein in the baculovirus expression system, using standard methods, such as those described in Summers et al, *A MANUAL OF METHODS FOR BACULOVIRUS VECTORS AND INSECT CELL CULTURE PROCEDURES*, Texas Agricultural Station Bulletin No. 1555 (1987). This expression vector contains the strong polyhedrin promoter of the Autographa californica nuclear polyhedrosis virus (AcMNPV) followed by convenient restriction sites. The signal peptide of AcMNPV gp67, including the N-terminal methionine, is located just upstream of a EcoRI site. The polyadenylation site of SV40 is used for efficient polyadenylation. For an easy selection of recombinant virus the beta-galactosidase gene from *E.coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzymes EcoRI and EcoRV and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E.coli* HB101 cells are transformed with ligation mix and spread on culture plates. Bacteria are identified that contain the plasmid with the human REQUIEM gene by digesting DNA from individual colonies using EcoRI and EcoRV and then analyzing the digestion product by gel electrophoresis. The seduce of the cloned fragment is confirmed by DNA sequencing. This plasmid is designated herein pBacREQUIEM.

5 µg of the plasmid pBacREQUIEM is co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417 (1987). 1 µg of BaculoGold™ virus DNA and 5 µg of the plasmid pBacREQUIEM are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf tube. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted REQUIEM is identified by DNA analysis including restriction mapping and sequencing. This is designated herein as V-REQUIEM.

Sf9 cells are grown in Grace's medium supplemented with 10% heat-inactivated FBS. The cells are infected with the recombinant baculovirus V-REQUIEM at a multiplicity of infection ("MOI") of about 2 (about 1 to about 3). Six hours later the medium is removed and is replaced with SF900 II medium minus methionine and cystine (available from Life Technologies Inc., Gaithersburg). 42 hours later, 5 µCi of $^{35}$S-methionine and 5 µCi of $^{35}$S cysteine (available from Amersham) are added. The cells are further incubated for 16 hours and then they are harvested by centrifugation, lysed and the labeled proteins are visualized by SDS-PAGE and autoradiography.

Example 3

Expression of REQUIEM in COS Cells

The expression plasmid, REQUIEM HA, is made by cloning a cDNA encoding REQUIEM into the expression vector pcDNAI/Amp (which can be obtained from Invitrogen, Inc.).

The expression vector pcDNAI/amp contains: (1) an *E.coli* origin of replication effective for propagation in *E. coli* and other prokaryotic cell; (2) an ampicillin resistance gene for selection of plasmid-containing prokaryotic cells; (3) an SV40 origin of replication for propagation in eucaryotic cells; (4) a CMV promoter, a polylinker, an SV40 intron, and a polyadenylation signal arranged so that a cDNA conveniently can be placed under expression control of the CMV promoter and operably lined to the SV40 intron and the polyadenylation signal by means of restriction sites in the polylinker.

A DNA fragment encoding the entire REQUIEM precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection of the recombinant protein with an antibody that recognizes the HA.

The plasmid construction strategy is as follows.

The REQUIEM cDNA of the clone from a cDNA library is amplified using primers that contained convenient restriction sites, much as described above regarding the construction of expression vectors for expression of REQUIEM in *E. coli* and *S. fugiperda*.

To facilitate detection, purification and characterization of the expressed REQUIEM, one of the primers contains a hemagglutinin tag ("HA tag") as described above.

Suitable primers include that following, which are used in this example.

The 5' primer, containing the underlined EcoRI site, an AUG start codon and 6 codons thereafter, forming the hexapeptide haemaglutinin tag, has the following sequence; 5' ATAACGA GAATTCATGGCGGCTGTGGTGGAAAATG 3' (SEQ ID NO:3)

The 3' primer, containing the underlined EcoRV site and 20 bp of 3' coding sequence (at the 3' has the following sequence; 5' ACGTCTAGA GATATCCACATCAAGAGGAGTTCTGG 3' (SEQ ID NO:4)

The PCR amplified DNA fragment and the vector, pcDNAI/Amp, are digested with and then ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolate from resistant colonies and examined by restriction analysis and gel sizing for the presence of the REQUIEM-encoding fragment.

For expression of recombinant REQUIEM, COS cells are transfected with an expression vector, as described above, using DEAE-DEXTRAN, as described, for instance, in Sambrook et al., cited above.

Cells are incubated under conditions for expression of REQUIEM by the vector.

Expression of the REQUIEM HA fusion protein is detected by radiolabelling and immunoprecipitation, using methods described in, for example Harbor et al., *ANTIBODIES: A LABORATORY MANUAL*, 2nd Ed.; Cold Spring Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Gene Therapeutic Expression of Human REQUIEM

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene by is digested with restriction enzymes for cloning a fragment to be expressed. The digested vector is treated with calf intestinal phosphatase to prevent self-ligation. The dephosphorylated, linear vector is fractionated on an agarose gel and purified.

REQUIEM cDNA capable of expressing active REQUIEM, is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the REQUIEM fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the REQUIEM gene is introduced into the packaging cells by standard techniques. Infectious viral particles containing the REQUIEM gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce REQUIEM product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated polypeptide comprising an amino acid sequence that is at least 95% identical to the amino acid sequence of SEQ ID NO:2.

2. An isolated polypeptide comprising the amino acid sequence set forth in SEQ ID NO:2.

3. An isolated polypeptide consisting of the amino acid sequence set forth in SEQ ID NO:2.

* * * * *

SEQUENCE LISTING

<160> NUMBER OF SEQ ID NOS: 5

<210> SEQ ID NO 1
<211> LENGTH: 1556
<212> TYPE: DNA
<213> ORGANISM: HOMO SAPIENS

<400> SEQUENCE: 1

```
ggcacgaggg aacagggaag atggcggctg tggtggaaaa tgtagtgaag ctccttgggg      60
agcagtacta caaagatgcc atggagcagt gccacaatta caatgctcgc ctctgtgctg     120
agcgcagcgt gcgcctgcct ttcttggact cacagaccgg agtagcccag agcaattgtt     180
acatctggat ggaaaagcga caccgggtc caggattggc ctccggacag ctgtactcct      240
accctgcccg gcgctggcgg aaaaagcggc gagcccatcc ccctgaggat ccacgacttt     300
ccttcccatc tattaagcca gacacagacc agaccctgaa gaaggagggg ctgatctctc     360
aggatggcag tagtttagag gctctgttgc gcactgaccc cctggagaag cgaggtgccc     420
```

-continued

```
cggatcccg agttgatgat gacagcctgg gcgagtttcc tgtgaccaac agtcgagcgc      480
gaaagcggat cctagaacca gatgacttcc tggatgacct cgatgatgaa gactatgaag      540
aagatactcc caagcgtcgg ggaaagggga atccaagggt aagggtgtg gcagtgccc      600 gtaagaagct ggatgcttcc atcctggagg accgggataa gccctatgcc tgtgacaata      660
gtttcaaaca aaagcatacc tcgaaagcgc cccagagagt ttgtggaaaa cgttacaaga      720
accgaccagg cctcagttac cactatgccc actcccactt ggctgaggag gagggcgagg      780
acaaggaaga ctctcaacca cccactcctg tttcccagag gtctgaggag cagaaatcca      840
aaaagggtcc tgatggattg gccttgccca caaactactg tgacttctgc ctgggggact      900
caaagattaa caagaagacg ggacaacccg aggagctggt gtcctgttct gactgtggcc      960
gctcagggca tccatcttgc ctccaattta ccccgtgat gatggcggca gtgaagacat     1020
accgctggca gtgcatcgag tgcaaatgtt gcaatatctg cggcacctcc gagaatgacg     1080
accagttgct cttctgtgat gactgcgatc gtggctacca catgtactgt ctcacccgt     1140 ccatgtctga gccccctgaa ggaagttgga gctgccacct gtgtctggac tgttgaaag     1200 agaaagcttc catctaccag aaccagaact cctcttgatg tggccaccca cctgctcccc     1260
gacatatcta aggctgtttc tctcctccac ttcatatttc ataccatct ttcccttctt     1320 cctcctctcc ttcacaaatc cagagaacct tggggtggtt gtgccagcct gcctttggca     1380
gctgcaagct gaggtggcag ctctgaccac ctctggcccc aggccctcca gggagaaagg     1440
agcaacacac tgcccctagg cgtgcgtgtg gcccagtttc tctctgctct ccattaagtg     1500
cattcactct gcttgccttg ggcccagccc cctggttgat tacagggttc aaggga        1556

<210> SEQ ID NO 2
<211> LENGTH: 405
<212> TYPE: PRT
<213> ORGANISM: HOMO SAPIENS

<400> SEQUENCE: 2

Met Ala Ala Val Val Glu Asn Val Val Lys Leu Leu Gly Glu Gln Tyr
1               5                  10                  15

Tyr Lys Asp Ala Met Glu Gln Cys His Asn Tyr Asn Ala Arg Leu Cys
            20                  25                  30

Ala Glu Arg Ser Val Arg Leu Pro Phe Leu Asp Ser Gln Thr Gly Val
        35                  40                  45

Ala Gln Ser Asn Cys Tyr Ile Trp Met Glu Lys Arg His Arg Gly Pro
    50                  55                  60

Gly Leu Ala Ser Gly Gln Leu Tyr Ser Tyr Pro Ala Arg Arg Trp Arg
65                  70                  75                  80

Lys Lys Arg Arg Ala His Pro Pro Glu Asp Pro Arg Leu Ser Phe Pro
                85                  90                  95

Ser Ile Lys Pro Asp Thr Asp Gln Thr Leu Lys Lys Glu Gly Leu Ile
            100                 105                 110

Ser Gln Asp Gly Ser Ser Leu Glu Ala Leu Leu Arg Thr Asp Pro Leu
        115                 120                 125

Glu Lys Arg Gly Ala Pro Asp Pro Arg Val Asp Asp Asp Ser Leu Gly
    130                 135                 140

Glu Phe Pro Val Thr Asn Ser Arg Ala Arg Lys Arg Ile Leu Glu Pro
145                 150                 155                 160

Asp Asp Phe Leu Asp Asp Leu Asp Asp Glu Asp Tyr Glu Glu Asp Thr
                165                 170                 175
```

-continued

```
Pro Lys Arg Arg Gly Lys Gly Lys Ser Lys Gly Lys Gly Val Gly Ser
            180                 185                 190

Ala Arg Lys Lys Leu Asp Ala Ser Ile Leu Glu Asp Arg Asp Lys Pro
        195                 200                 205

Tyr Ala Cys Asp Asn Ser Phe Lys Gln Lys His Thr Ser Lys Ala Pro
    210                 215                 220

Gln Arg Val Cys Gly Lys Arg Tyr Lys Asn Arg Pro Gly Leu Ser Tyr
225                 230                 235                 240

His Tyr Ala His Ser His Leu Ala Glu Glu Gly Glu Asp Lys Glu
                245                 250                 255

Asp Ser Gln Pro Pro Thr Pro Val Ser Gln Arg Ser Glu Glu Gln Lys
            260                 265                 270

Ser Lys Lys Gly Pro Asp Gly Leu Ala Leu Pro Asn Asn Tyr Cys Asp
        275                 280                 285

Phe Cys Leu Gly Asp Ser Lys Ile Asn Lys Lys Thr Gly Gln Pro Glu
    290                 295                 300

Glu Leu Val Ser Cys Ser Asp Cys Gly Arg Ser Gly His Pro Ser Cys
305                 310                 315                 320

Leu Gln Phe Thr Pro Val Met Met Ala Val Lys Thr Tyr Arg Trp
                325                 330                 335

Gln Cys Ile Glu Cys Lys Cys Asn Ile Cys Gly Thr Ser Glu Asn
            340                 345                 350

Asp Asp Gln Leu Leu Phe Cys Asp Cys Asp Arg Gly Tyr His Met
            355                 360                 365

Tyr Cys Leu Thr Pro Ser Met Ser Glu Pro Pro Glu Gly Ser Trp Ser
    370                 375                 380

Cys His Leu Cys Leu Asp Leu Leu Lys Glu Lys Ala Ser Ile Tyr Gln
385                 390                 395                 400

Asn Gln Asn Ser Ser
                405

<210> SEQ ID NO 3
<211> LENGTH: 35
<212> TYPE: DNA
<213> ORGANISM: HOMO SAPIENS

<400> SEQUENCE: 3
ataacgagaa ttcatggcgg ctgtggtgga aaatg                              35

<210> SEQ ID NO 4
<211> LENGTH: 35
<212> TYPE: DNA
<213> ORGANISM: HOMO SAPIENS

<400> SEQUENCE: 4
acgtctagag atatccacat caagaggagt tctgg                              35

<210> SEQ ID NO 5
<211> LENGTH: 371
<212> TYPE: PRT
<213> ORGANISM: MURINE

<400> SEQUENCE: 5

Met Glu Gln Cys His Asn Tyr Asn Ala Arg Leu Cys Ala Glu Arg Ser
1               5                   10                  15

Val Arg Leu Pro Phe Leu Asp Ser Gln Thr Gly Val Ala Gln Ser Asn
            20                  25                  30
```

-continued

```
Cys Tyr Ile Trp Met Glu Lys Arg His Arg Gly Pro Gly Leu Ala Ser
        35                  40                  45

Gly Gln Leu Tyr Ser Tyr Pro Ala Arg Arg Trp Arg Lys Lys Arg Arg
        50                  55                  60

Ala His Pro Pro Glu Asp Pro Arg Leu Ser Phe Pro Ser Ile Lys Pro
65                  70                  75                  80

Asp Thr Asp Gln Thr Leu Lys Lys Glu Gly Leu Ile Ser Gln Asp Gly
                85                  90                  95

Ser Ser Leu Glu Ala Leu Leu Arg Thr Asp Pro Leu Glu Lys Arg Gly
                100                 105                 110

Ala Pro Asp Pro Arg Val Asp Asp Ser Leu Gly Glu Phe Pro Val
                115                 120                 125

Ser Asn Ser Arg Ala Arg Lys Arg Ile Ile Glu Pro Asp Asp Phe Leu
        130                 135                 140

Asp Asp Leu Asp Asp Glu Asp Tyr Glu Glu Asp Arg Pro Lys Arg Arg
145                 150                 155                 160

Gly Lys Gly Lys Ser Lys Ser Lys Gly Val Ser Ser Ala Arg Lys Lys
                165                 170                 175

Leu Asp Ala Ser Ile Leu Glu Asp Arg Asp Lys Pro Tyr Ala Cys Asp
                180                 185                 190

Ile Cys Gly Lys Arg Tyr Lys Asn Arg Pro Gly Leu Ser Tyr His Tyr
        195                 200                 205

Ala His Ser His Leu Ala Glu Glu Gly Glu Asp Lys Glu Asp Ser
        210                 215                 220

Arg Pro Pro Thr Pro Val Ser Gln Arg Ser Glu Glu Gln Lys Ser Lys
225                 230                 235                 240

Lys Gly Pro Asp Gly Leu Ala Leu Pro Asn Asn Tyr Cys Asp Phe Cys
                245                 250                 255

Leu Gly Asp Ser Lys Ile Asn Lys Lys Thr Gly Gln Pro Glu Glu Leu
                260                 265                 270

Val Ser Cys Ser Asp Cys Gly Arg Ser Gly His Pro Ser Cys Leu Gln
        275                 280                 285

Phe Thr Pro Val Met Met Ala Ala Val Lys Thr Tyr Arg Trp Gln Cys
        290                 295                 300

Ile Glu Cys Lys Cys Cys Asn Leu Cys Gly Thr Ser Glu Asn Asp Asp
305                 310                 315                 320

Gln Leu Leu Phe Cys Asp Asp Cys Asp Arg Gly Tyr His Met Tyr Cys
                325                 330                 335

Leu Thr Pro Ser Met Ser Glu Pro Pro Glu Gly Ser Trp Ser Cys His
                340                 345                 350

Leu Cys Leu Asp Leu Leu Lys Glu Lys Ala Ser Ile Tyr Gln Asn Gln
        355                 360                 365

Asn Ser Ser
        370
```